United States Patent
Di Girolamo et al.

(10) Patent No.: US 8,134,039 B2
(45) Date of Patent: Mar. 13, 2012

(54) PROCESS FOR THE PRODUCTION OF HIGH-OCTANE HYDROCARBON COMPOUNDS BY THE SELECTIVE DIMERIZATION OF ISOBUTENE CONTAINED IN A STREAM WHICH ALSO CONTAINS $C_5$ HYDROCARBONS

(75) Inventors: Marco Di Girolamo, San Donato Milanese-Milan (IT); Domenico Sanfilippo, Paullo-Milan (IT); Massimo Conte, Peschiera Borromeo-Milan (IT)

(73) Assignee: Snamprogetti S.p.A., San Donato Milanese (IT)

( * ) Notice: Subject to any disclaimer, the term of this patent is extended or adjusted under 35 U.S.C. 154(b) by 599 days.

(21) Appl. No.: 12/090,398

(22) PCT Filed: Nov. 14, 2006

(86) PCT No.: PCT/EP2006/010895
§ 371 (c)(1),
(2), (4) Date: Apr. 16, 2008

(87) PCT Pub. No.: WO2007/057153
PCT Pub. Date: May 24, 2007

(65) Prior Publication Data
US 2008/0242909 A1    Oct. 2, 2008

(30) Foreign Application Priority Data
Nov. 17, 2005    (IT) .............................. MI2005A2199

(51) Int. Cl.
*C07C 1/20*    (2006.01)

(52) U.S. Cl. ........ 585/639; 585/255; 585/310; 585/316; 585/510; 585/520; 585/526; 585/527; 44/449; 44/450

(58) Field of Classification Search ................. 585/255, 585/310, 316, 510, 520, 526, 527, 639; 44/449, 44/450
See application file for complete search history.

(56) References Cited

U.S. PATENT DOCUMENTS

| | | |
|---|---|---|
| 4,100,220 A | 7/1978 | Bowman et al. |
| 5,003,124 A | 3/1991 | Smith, Jr. et al. |
| 5,723,687 A | 3/1998 | Marchionna et al. |
| 6,011,191 A | 1/2000 | Di Girolamo et al. |
| 6,433,238 B1 | 8/2002 | Di Girolamo et al. |
| 6,500,999 B2 | 12/2002 | Di Girolamo et al. |
| 6,613,108 B1 * | 9/2003 | Aittamaa et al. ................ 44/449 |
| 6,897,345 B2 | 5/2005 | Marchionna et al. |
| 7,339,086 B2 | 3/2008 | Di Gerolamo et al. |
| 2002/0087040 A1 | 7/2002 | Marchionna et al. |
| 2005/0077211 A1 | 4/2005 | Catani et al. |

FOREIGN PATENT DOCUMENTS

| | | |
|---|---|---|
| WO | 03 033442 | 4/2003 |
| WO | 2005 040312 | 5/2005 |

* cited by examiner

*Primary Examiner* — Prem C Singh
(74) *Attorney, Agent, or Firm* — Oblon, Spivak, McClelland, Maier & Neustadt, L.L.P.

(57) ABSTRACT

A process is described for the production of high-octane hydrocarbon compounds by means of the selective dimerization of isobutene, in the presence of $C_5$ hydrocarbons and oxygenated compounds (branched alcohols or alternatively blends of linear or branched alcohols and alkyl ethers) characterized in that it utilizes a catalytic distillation as second reaction step.

32 Claims, 7 Drawing Sheets

PROCESS FOR THE PRODUCTION OF HIGH-OCTANE HYDROCARBON COMPOUNDS BY THE SELECTIVE DIMERIZATION OF ISOBUTENE CONTAINED IN A STREAM WHICH ALSO CONTAINS $C_5$ HYDROCARBONS

The present invention relates to a process for the production of high-octane hydrocarbon compounds by means of the selective dimerization of isobutene and, to a lesser extent, of possible linear olefins, in the presence of $C_5$ hydrocarbons and oxygenated compounds, which favour the formation of higher selectivities on the part of the catalyst.

The mixture obtained can then be hydrogenated with conventional methods to obtain a product with further enhanced octane characteristics.

For mainly environmental reasons, the composition of gasolines is being reformulated and the general tendency is towards the production of fuels which burn better and have lower evaporative emissions. The main measures for achieving this objective are listed below (D. Sanfilippo, F. Ancillotti, M. Marchionna, Chim. & Ind., 76, (1994), 32):

reduction in the content of aromatic compounds and elimination of benzene;
reduction in the volatility of gasolines to minimize evaporative losses;
reduction in the content of light olefins, photochemically extremely reactive;
reduction in the sulfur content and final boiling point of the gasolines.

All these measures consequently create the necessity of projecting new production processes of purely hydrocarbon compounds capable of positively contributing to the above demands.

Among these, alkylated products are extremely important as they have a high octane number, a low volatility and are practically free of olefins and aromatic compounds. The alkylation process in liquid phase is a reaction between isoparaffinic hydrocarbons, such as isobutane, and olefins, for example propylene, butenes, pentenes and relative mixtures, in the presence of an acid catalyst for the production of $C_7$-$C_9$ hydrocarbons with a high octane number to be used in gasolines (A. Corma, A. Martinez, Catal. Rev.—Sci. Eng., 35, (1993), 483).

The main problem of alkylation processes is due to the fact that, with growing environmental regulations, both of the traditional processes (with hydrofluoric and sulfuric acid) are encountering considerable difficulties, which create uncertainties for the future; the process with hydrofluoric acid due to the toxicity of this acid, especially in populated areas, and that using sulfuric acid, as a result of the large production of acid sludge as well as the considerably corrosive nature of the catalyst.

Alternative processes with solid acid catalysts are being developed but their commercial applicability has yet to be demonstrated.

A hydrocarbon product of this type, on the other hand, is becoming increasingly more requested due to its octane characteristics (both the Research Octane Number (RON) and the Motor Octane Number (MON) are high) and those relating to the boiling point (limited volatility but low end-point) which position it in the group of compositions of great interest for obtaining gasolines which are more compatible with current environmental requirements.

An alternative refinery process for obtaining products with characteristics similar to those of alkylated products can be offered by the hydrogenation of so-called "polymer" gasoline.

Oligomerization processes (often inaccurately called polymerization in the refining industry) were widely used in the '30s' and '40s' for converting low-boiling $C_3$-$C_4$ olefins into gasolines. The process leads to the production of a gasoline with a high octane number (RON about 97) but with a high sensitivity (difference between RON and MON) due to the purely olefinic nature of the product (J. H. Gary, G. E. Handwerk, "Petroleum Refining: Technology and Economics", $3^{rd}$ Ed., M. Dekker, New York, (1994), 250).

Typical olefins which are oligomerized are mainly propylene, which gives dimers or slightly higher oligomers depending on the process used, and isobutene which mainly gives dimers but is always accompanied by a considerable quantity of higher oligomers.

With particular attention to the oligomerization of isobutene, it is known that this reaction can be carried out either batchwise, semi-batchwise or in continuous, either in gas or liquid phase, generally at temperatures ranging from 50 to 300° C. and at atmospheric pressure or such pressures as to maintain the reagents in liquid phase, if necessary.

Typical catalysts for the industrial oligomerization process of isobutene are represented by phosphoric acid, generally supported on a solid (for example kieselguhr), or cation-exchange acid resins. The latter allow blander conditions to be used compared with supported phosphoric acid both in terms of temperature and pressure (50-100° C. and 0.2-3 MPa with respect to 200-220° C. and 3-10 MPa).

Other catalysts are also claimed in literature, both liquid acids such as $H_2SO_4$ and derivatives of sulfonic acids, and solids such as silico-aluminas, mixed oxides, zeolites, fluorinated or chlorinated aluminas, etc.; none of these catalysts however has so far enabled an industrial process to be set up, as in the case of supported phosphoric acid (F. Asinger, "Mono-olefins: Chemistry and Technology", Pergamon Press, Oxford, pages 435-456) and that of cation resins (G. Scharfe, Hydrocarbon Proc., April 1973, 171).

From the product point of view, the main problem of this process lies in the fact that excessive percentages of heavy oligomers such as trimers (selectivity of 20-40%) and tetramers (selectivity of 1-5%) of isobutene, are produced in the oligomerization phase. Tetramers are completely outside the gasoline fraction as they are too high-boiling and therefore represent a net loss in yield to gasoline; as far as trimers are concerned, their concentration should be greatly reduced as they have a boiling point (170-180° C.) at the limit of future specifications on the final point of reformulated gasolines.

The problem of reducing the formation of oligomers higher than dimers to percentages lower than 15% is, on the other hand, a problem typical of the oligomerization of isobutene, as also indicated in literature (C. T. O'Connor, M. Kojima, K. W. Shcumann, Appl. Catal., 16, (1985), 193). This level of heavy compounds is slightly higher than that of an alkylated product and is still tolerated in the gasoline pool.

From what is specified above, there is evidently great interest in obtaining a new dimerization process of isobutene which allows the synthesis of a higher-quality product, through reaching greater selectivities.

By carrying out the selective dimerization reaction of isobutene in the presence of moderate quantities of oxygenated products, the production of a fraction of oligomers is selectively obtained, which is particular rich in dimers (>85%) and practically free of tetramers and higher oligomers (<0.5%).

The reaction product is then preferably hydrogenated to give a completely saturated end-product with a high octane number and low sensitivity.

The hydrogenation can be carried out with conventional methods as described, for example, in F. Asinger, "Mono-olefins: Chemistry and Technology", Pergamon Press, Oxford, page 455.

SUMMARY OF THE INVENTION

One embodiment of the invention includes a process for producing high-octane hydrocarbon compositions by dimerizing isobutene in the presence of $C_5$ hydrocarbons and oxygenated compounds utilizing a catalytic distillation as reaction step. In another embodiment the dimerizing is carried out in the presence of moderate quantities of oxygenated products to form an oligomer fraction that is particular rich in dimers and practically free of tetramers and higher oligomers.

In other embodiments the process includes producing high-octane hydrocarbon compounds by selectively dimerizing isobutene in mixtures comprising $C_5$ hydrocarbons such that (i) the reaction is carried out in two distinct steps and (ii) a catalytic distillation is used as second step; and wherein the dimerizing is carried out in the presence of oxygenated products selected from a branched alcohol alone or in a blend with linear alcohols and alkyl ethers, in such a quantity as to have in the feeding, in the case of the presence of a branched alcohol alone, a molar ratio oxygenated product/isobutene higher than 0.005, in the case of the presence of a branched alcohol in a blend, a molar ratio oxygenated product/isobutene higher than 0.01.

Figure 1:
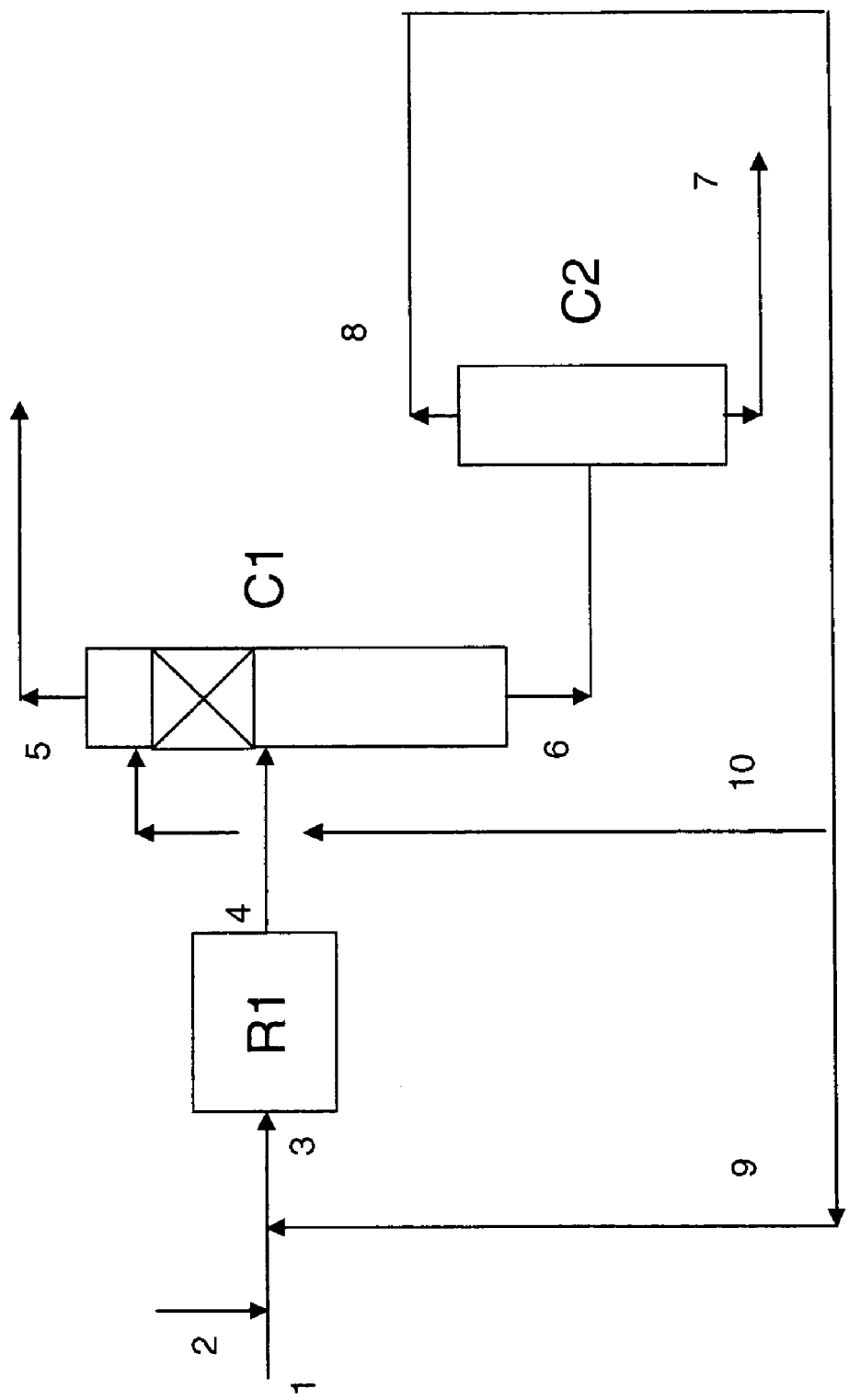
FIG. 1 shows a process scheme with catalytic distillation where $C_5$ products are not present in the charge and the oxygenated product is a branched alcohol.

For illustrative purposes, Table 1 indicates the octane number and relative boiling points of some of the products obtained, by means of the process, object of the present invention.

TABLE 1

| Product | RON | MON | b.p. (° C.) |
|---|---|---|---|
| Diisobutenes | 100 | 89 | 100-105 |
| Iso-octane | 100 | 100 | 99 |
| Tri-isobutenes | 100 | 89 | 175-185 |
| Hydrogenated tri-isobutenes | 101 | 102 | 170-180 |

The process, object of the present invention, for the production of high-octane hydrocarbon compounds by the selective dimerization of isobutene contained in a stream also containing $C_5$ hydrocarbons, is characterized in that:

the reaction is carried out in two distinct steps,
a catalytic distillation is used as second step,
the reaction is carried out in the presence of oxygenated products selected from a branched alcohol alone or in a blend with linear alcohols and alkyl ethers, in such a quantity as to have in the feeding, in the case of the presence of a branched alcohol alone, a molar ratio oxygenated product/isobutene higher than 0.005, in the case of the presence of a branched alcohol in a blend, a molar ratio oxygenated product/isobutene higher than 0.01.

It should also be pointed out that in the case of hydrocarbon streams also comprising other olefins, it has been observed that at least a part of the latter can be converted by reaction with isobutene into the hydrocarbon product without altering the octane value. It is therefore preferable to effect an enriching treatment, by means of pre-isomerization, of the internal linear olefins, in order to favour the overall octane number of the mixture.

The process claimed herein can be applied to cuts mainly containing isobutane, isobutene, n-butane, n-butenes and saturated and olefinic $C_5$ hydrocarbons.

Although a wide variety of sources are available for the supply of these streams, the most common are those deriving from Dehydrogenation processes of iso-paraffins, from FCC units, Steam Cracking or processes for the production of pure isobutene such as the dehydration of tert-butyl alcohol (TBA) or the Cracking of MTBE and/or ETBE; these streams differ from each other in the content of isobutene and linear butenes, as shown in Table 2.

TABLE 2

|  | Steam Cracking | FCC | Dehydrogenation | Pure isobutene |
|---|---|---|---|---|
| Isobutene | 30-50 | 10-25 | 45-55 | >90 |
| n-butenes | 35-60 | 25-50 | 1-2 | <10 |
| Saturated $C_4$ | 4-10 | 30-60 | 45-55 | <1 |

Should streams from Steam Cracking contain diolefins in addition to the desired mono-olefins, they must be eliminated by means of typical removal treatment (for example solvent extraction or selective hydrogenation).

Saturated and olefinic $C_5$ hydrocarbons can be present in these streams, in various amounts (0.2-20%), depending on the efficiency of the $C_4$-$C_5$ separation step. The $C_5$ olefins possibly present can be involved in dimerization reactions.

The stream sent to the reaction steps can contain branched alcohols or a blend of alcohols and alkyl ethers, in addition to the hydrocarbon components.

The linear alcohols used contain a number of carbon atoms ranging from 1 to 6 and those preferred are methanol and/or ethanol. The branched alcohols have from 3 to 6 carbon atoms and those preferred are tert-butyl alcohol (TBA) and/or tert-amyl alcohol (TAA).

The alkyl ether used can be selected from those containing a number of carbon atoms ranging from 5 to 10: MTBE (methyl tert-butyl ether), ETBE (ethyl tert-butyl ether), MSBE (methyl sec-butyl ether), ESBE (ethyl sec-butyl ether), TAME (methyl tert-amyl ether), TAEE (ethyl tert-amyl ether) or mixtures thereof are preferred.

Isobutene, together with the hydrocarbon stream in which it is contained, is sent with the oxygenated products, in stoichiometric defect, into contact with the acid catalyst where the dimerization takes place. The linear primary alcohol, possibly present, in addition to interacting with the catalysts, also helps to limit the possible cracking of the alkyl ether and can possibly react with the dimers and linear $C_4$ olefins, whereas the branched alcohol (tertiary) does not react with the olefins due to its steric hindrance.

In order to obtain the dimerization product with the desired selectivity to dimers, it is essential to maintain a constant level of oxygenated products in the reaction environment to form the catalytic species with the correct activity and stability. The optimal level of oxygenated products present in the reaction environment, to obtain selectivities to dimers close to 85% by weight, depends on the composition of the hydrocarbon charge. The higher the olefin content in the charge, the lower the amount of oxygenated products to be used.

A wide variety of acid catalysts can be used for this process, but those preferred are styrene-divinyl benzene polymeric resins having sulphonic groups as catalytic centres.

A large range of operative conditions can be used to produce high-octane hydrocarbons from isobutene in the desired selectivities. It is possible to operate in vapour or liquid-vapour phase, but operating conditions in liquid phase are preferred.

The pressure is preferably higher than the atmospheric value, in order to maintain the reagents in liquid phase, generally below 5 MPa, more preferably between 0.2-2.5 MPa. The reaction temperature preferably ranges from 30 to 120° C.

The feeding space velocities of the oxygenated-hydrocarbon stream are preferably lower than 30 $h^{-1}$, more preferably ranging from 1 and 15 $h^{-1}$.

Isobutene is mainly converted in the reaction zone, however portions of the other paraffins which are present can also be converted to useful product; in principle, there are no limits to the concentration of iso-olefin in the hydrocarbon fraction, even if concentrations ranging from 2 to 60% are preferred; in case of streams having a high isobutene concentration (dehydration or cracking) it is therefore convenient to dilute the charge with $C_4$-$C_7$ hydrocarbons. There are no limits, on the contrary, for the ratio between isobutene and linear olefins.

The process, object of the present invention, can be effected batchwise or in continuous, bearing in mind however that the latter is much more advantageous in industrial practice.

The reactor configuration selected includes a first reaction step (one or more fixed bed reactors) and a second step consisting of a catalytic distillation which avoids the use of a reactor and a distillation column, as in a conventional plant.

The presence of $C_5$ hydrocarbons in the feed, however, complicates the process schemes, as these compounds have intermediate boiling temperatures between $C_4$ and oxygenated products, and they also form azeotropic mixtures with the branched alcohols as shown in Table 3, which indicates the boiling points of the most representative low-boiling components present in the streams

TABLE 3

| Compound | Boiling point, ° C. |
|---|---|
| $C_4$/Methanol azeotropic product | −5 |
| $C_4$ products | −12/1 |
| Isopentane/TBA azeotropic product | 25 |
| Isopentane | 28 |
| 1-pentene | 30 |
| 2-methyl-1-butene | 31 |
| n-pentane | 36 |
| 2-methyl-2-butene | 39 |
| cyclopentane | 49 |
| MTBE | 55 |

TABLE 3-continued

| Compound | Boiling point, ° C. |
|---|---|
| Methanol | 65 |
| Dimers/TBA azeotropic product | 78 |
| TBA | 82 |
| Dimers | 100-105 |

The $C_5$ products cannot therefore be removed from the plant together with the $C_4$ products, as they would introduce oxygenated products (branched alcohols) into the stream, which are difficult to remove by means of the traditional techniques used for removing methanol (water washing) and which are poisonous for the subsequent treatment processes of the streams (polymerization, alkylation and metathesis).

The $C_5$ products, on the other hand, cannot be maintained in the oxygenated stream as they would rapidly accumulate. With respect to the schemes shown in literature (U.S. Pat. No. 6,011,191), it is therefore necessary to introduce a $C_5$/branched alcohol azeotropic separation step, which can be inserted in several positions of the plant, in relation to the $C_5$ content in the charge and also the relative concentration of the $C_5$ products present.

When the oxygenated product is a branched alcohol alone, the process is, in particular, preferably effected with a molar ratio of oxygenated product/isobutene lower than 0.6, through the following essential steps:

a) feeding the $C_4$-$C_5$ hydrocarbon cut containing isobutene to the first reaction step (consisting of one or more reactors), together with one or more streams containing oxygenated products;
b) using a catalytic distillation column as second reaction step, wherein the isobutene conversion is completed, in addition to the separation of the reagents/products;
c) recovering the $C_5$ hydrocarbon/branched alcohol azeotropic product, in one or more fractionation columns, also catalytic, as head stream, side cut or bottom stream;
d) recycling the stream containing the oxygenated products and possibly the reintegrated oxygenated products, to the two reaction steps;
e) possibly recycling part of the $C_4$ products to the first reaction step, in order to maximize the isobutene conversion.

The first reaction step can consist of one or more fixed bed, tubular and/or adiabatic reactors.

The separation of the $C_5$/branched alcohol azeotropic product of step (c) is preferably effected starting from blends:
  a) $C_5$—oxygenated products—reaction product, wherein the $C_5$ hydrocarbons are recovered as azeotropic compound with the branched alcohol, as head effluent, using a scheme based on one or two fractionation columns;
  b) $C_4$-$C_5$—oxygenated products—reaction product, wherein the $C_5$ hydrocarbons are recovered as azeotropic compound with the branched alcohol as side cut of a catalytic distillation column from whose head the $C_4$ products are recovered and at the bottom a blend containing the oxygenated products and the reaction product;
  c) $C_4$-$C_5$—oxygenated products, wherein the $C_5$ hydrocarbons are recovered as azeotropic compound with the branched alcohol as the bottom effluent of a fractionation column from whose head the $C_4$ products are recovered.

When the oxygenated product is a branched alcohol in a mixture with linear alcohols and alkyl ethers, the process is preferably effected, in particular, with a molar ratio of oxygenated product/isobutene lower than 0.7, by means of the following essential steps:

a) feeding the $C_4$-$C_5$ hydrocarbon cut containing isobutene to the first reaction step (consisting of one or more reactors), together with one or more streams containing oxygenated products (linear and branched alcohols, ethers and water);
b) using a catalytic distillation column as second reaction step, wherein the isobutene conversion is completed, in addition to the separation of the reagents/products;
c) separating the $C_4$/linear alcohol azeotropic product and possibly $C_4$ products from the remaining oxygenated compounds and from the hydrocarbon product, in one or more distillation columns, also catalytic;
d) recovering the linear alcohol from the azeotropic product with the $C_4$ compounds, by means of conventional processes such as water washing or adsorption on inorganic solids;
e) recovering the $C_5$/branched alcohol azeotropic product, in one or more fractionation columns, also catalytic, as head stream, side cut or bottom stream;
f) recycling the stream containing the oxygenated products (branched alcohol and ether) and possibly the reintegrated oxygenated products and recovered linear alcohol, to the two reaction steps;
g) possibly recycling part of the $C_4$ products to the first reaction step, in order to maximize the isobutene conversion.

The first reaction step can consist of one or more adiabatic reactors, such as traditional, boiling point, expanded bed reactors.

The separation of the $C_5$/branched alcohol azeotropic product of step (e) is preferably effected starting from blends of:
a) $C_5$—oxygenated products (ethers and branched alcohols)—reaction product, wherein the $C_5$ hydrocarbons are recovered as an azeotropic compound with the branched alcohol, as head effluent, using a scheme based on one (recovery of the remaining oxygenated products as side cut) or two fractionation columns;
b) $C_5$—oxygenated products (ethers and branched alcohols—dimers, in which the $C_5$ hydrocarbons are recovered as azeotropic product with the branched alcohol as head effluent of a fractionation column;
c) $C_4$-$C_5$—oxygenated products (ethers and linear and branched alcohols)—reaction product, effluent from a reaction step, wherein the $C_5$ hydrocarbons are recovered as an azeotropic compound with the branched alcohol as side cut of a fractionation column from whose head the $C_4$/linear alcohol azeotropic product and possibly the $C_4$ products are recovered, whereas a mixture containing the oxygenated products and the reaction product is recovered at the bottom;
d) $C_4$-$C_5$—oxygenated products (linear and branched alcohols) wherein the $C_5$ hydrocarbons are recovered as an azeotropic compound with the branched alcohol as bottom effluent of a fractionation column from whose head the $C_4$/linear alcohol azeotropic product and possibly $C_4$ products are recovered.

For the two processes comprising the essential steps specified above (a-e and a-g) the $C_5$ products are present in the streams prevalently containing $C_4$ products in a quantity preferably ranging from 0.5 to 10% by weight.

Seven process schemes are shown in FIGS. 1-7, in order to clearly illustrate the present invention.

FIG. 1 shows a process scheme with catalytic distillation, when $C_5$ products are not present in the charge and the oxygenated product is a branched alcohol (TBA).

The stream (1) containing isobutene, together with the reintegration feeding of TA (or possibly water) (2) and the recycled stream of oxygenated products (9), is sent to a first reaction step (R1), which can consist of one or more fixed bed reactors, in which the $C_4$ iso-olefin is selectively converted to dimers.

The effluent (4) from the first reaction step, is sent to a catalytic distillation (C1) in which the isobutene conversion is completed. A stream (5) essentially containing $C_4$ hydrocarbons is removed from the head of this column, whereas a stream (6) essentially containing the reaction product and the oxygenated compounds, is collected at the bottom.

This stream (6) is sent to a further separation column (C2) wherein a stream (8) is collected at the head, containing the dimers/TBA azeotropic product which is recycled to the two reaction steps (streams 9 and 10), whereas the reaction product (7) essentially consisting of dimers and trimers, is collected from the bottom.

Figure 2:
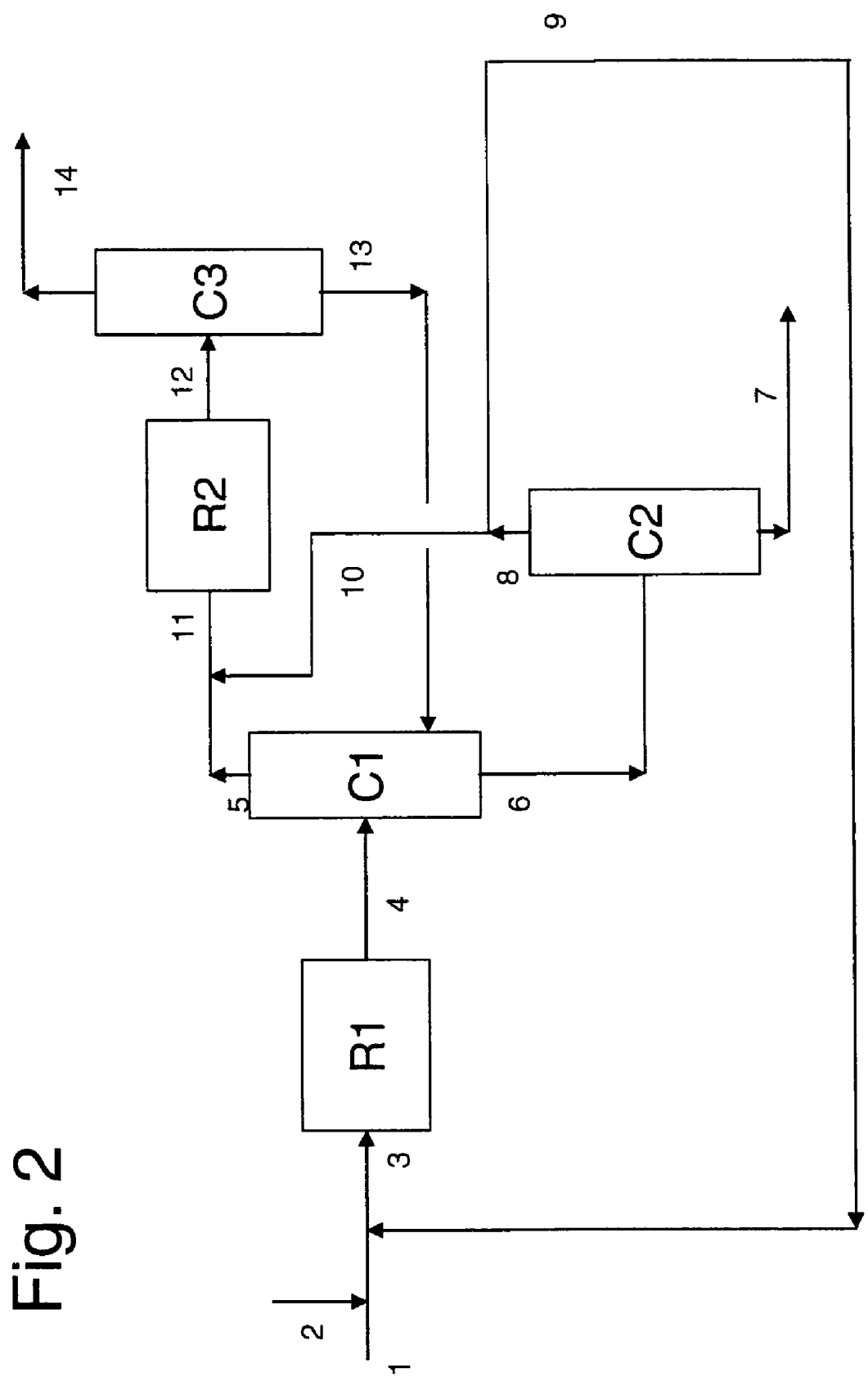
FIG. 2 shows a process scheme including a catalytic distillation, two reaction steps (fixed bed reactors) and three fractionation columns.

The introduction of catalytic distillation allows a considerable simplification of the plant scheme, which is instead based on two reaction steps (fixed bed reactors) and three fractionation columns, as shown in FIG. 2.

When $C_5$ hydrocarbons are present in the charge, different plant configurations can be used to recover the $C_5$/TBA azeotropic product, depending on the quantity of $C_5$ products present and the required purity of the streams.

Figure 3:
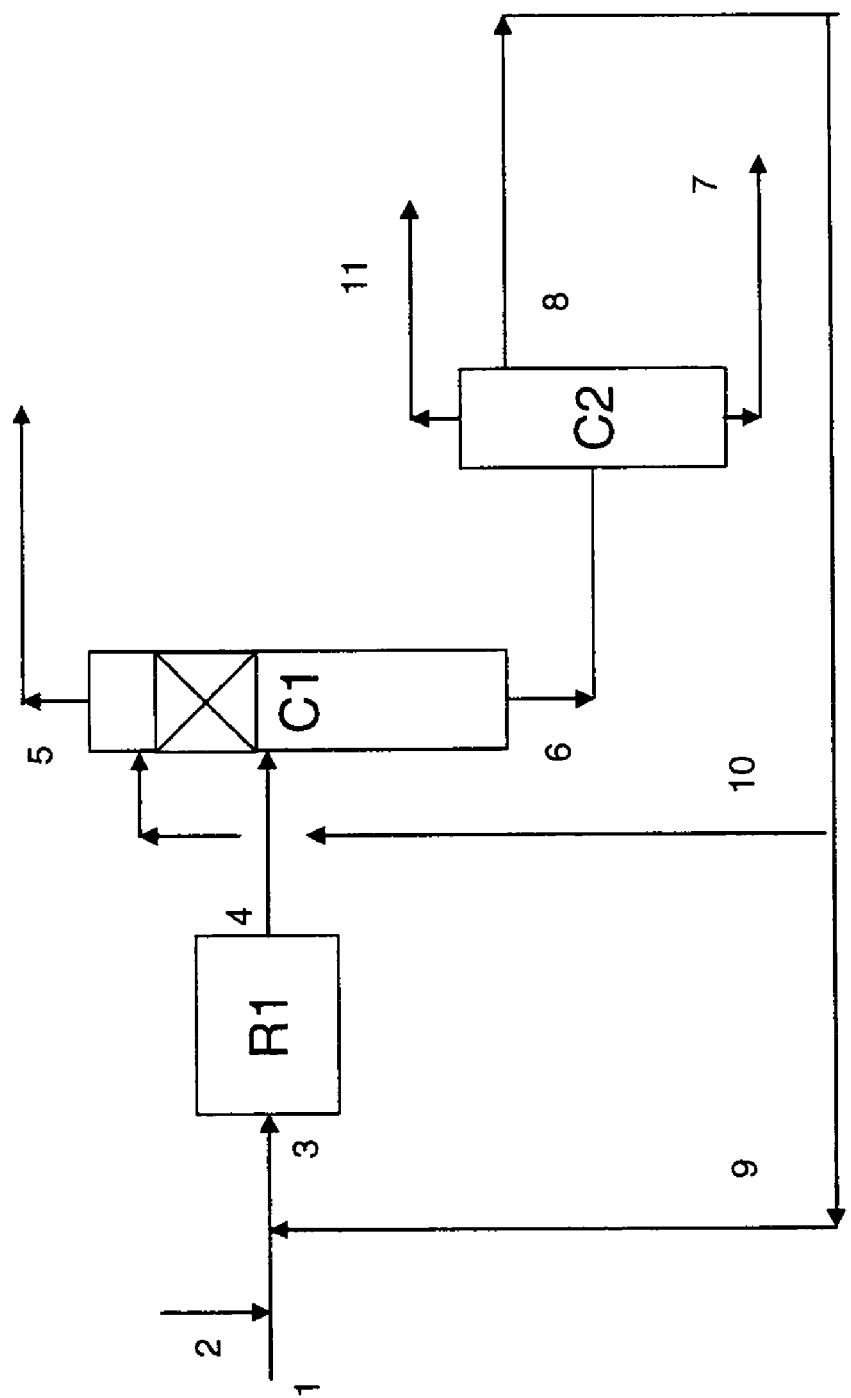
FIG. 3 shows a process scheme in which the $C_5$/TBA azeotropic product is recovered from the head of a column.

FIG. 3 shows a possible process scheme which differs from that of FIG. 1 due to the fact that the $C_5$/TBA azeotropic product (11) is recovered from the head of the column C2, which can possibly be joined to the reaction product, whereas the stream containing the oxygenated products to be recycled (TBA/dimers azeotropic product) is removed from the column C2 as side cut (8).

Figure 4:
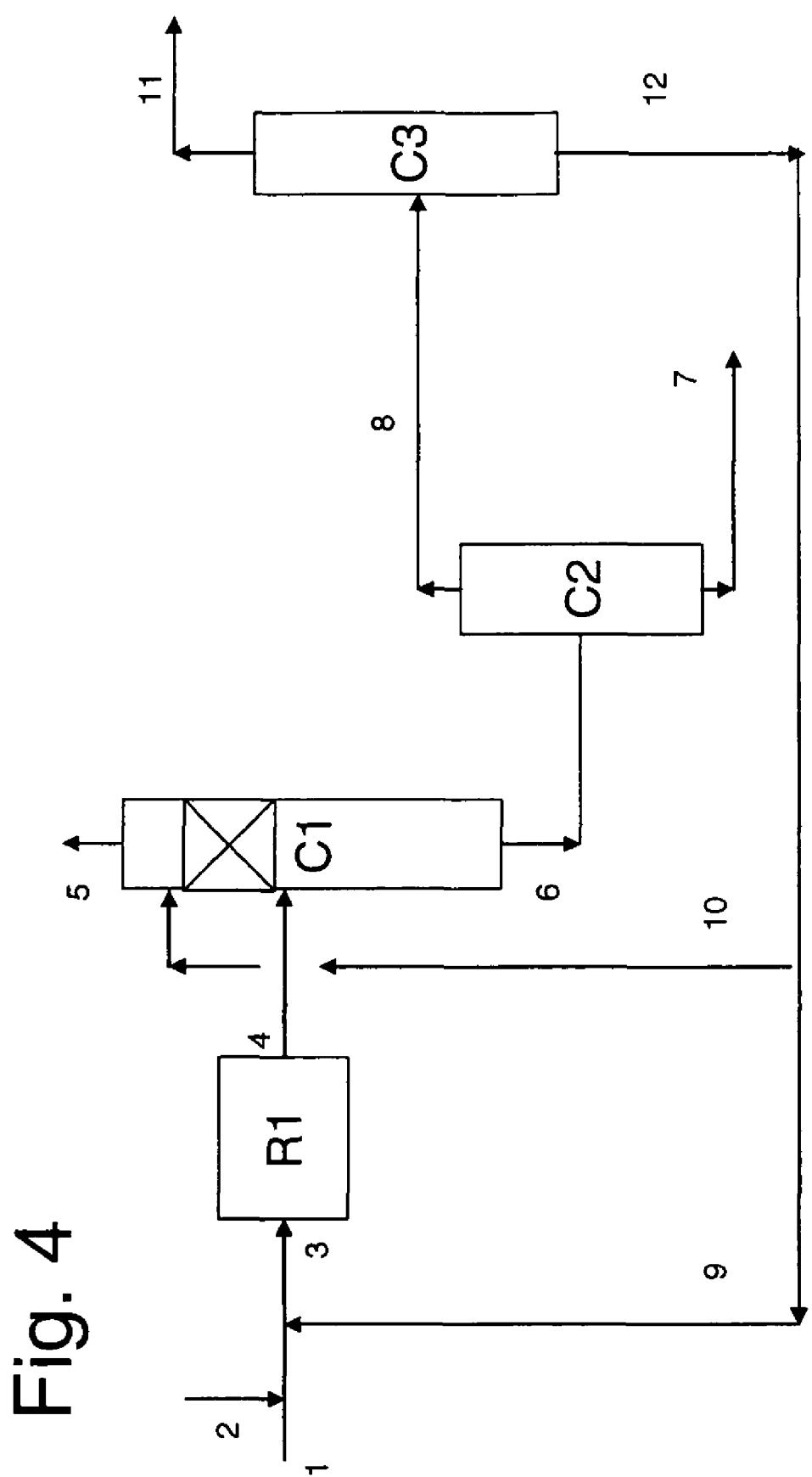
FIG. 4 shows a process scheme with a fractionation column.

The process scheme is more complex when a more efficient separation of the two $C_5$/TBA and dimers/TBA azeotropic products is to be effected, as a new fractionation column (C3) must be inserted, as shown in FIG. 4. In this new scheme, the head stream of the column C2 (8) is sent to a new column (C3) wherein the $C_5$/TBA azeotropic product (11) is separated at the head and the dimers/TBA azeotropic product (12) which is recycled to the two reaction steps (streams 9 and 10), is separated at the bottom.

Figure 5:
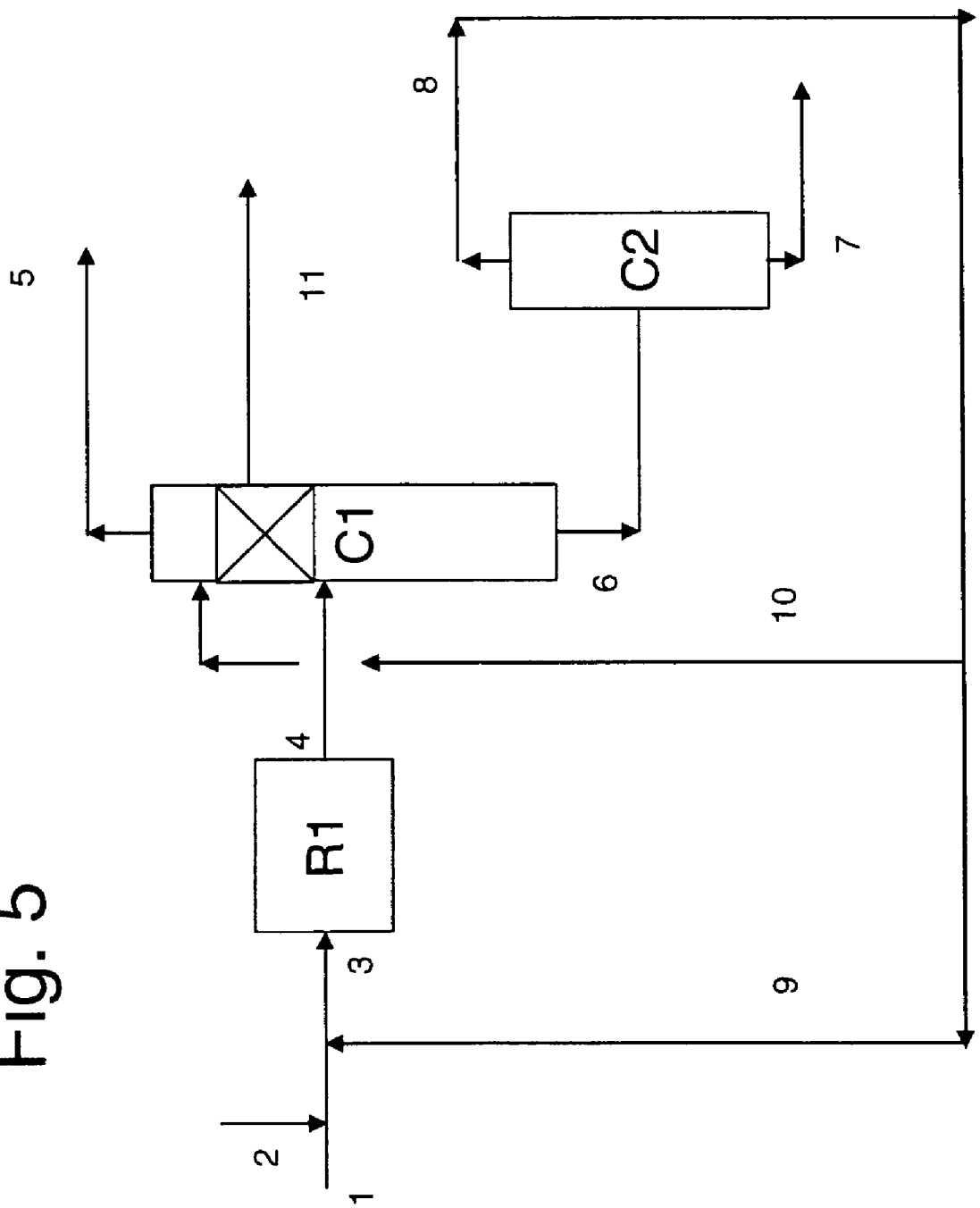
FIG. 5 shows a process scheme in which an $C_5$/TBA azeotropic product is recovered as a side cut in a column reactor.

Alternatively, the $C_5$/TBA azeotropic product can be recovered as side cut (11) in the column reactor C1 (FIG. 5).

Figure 6:
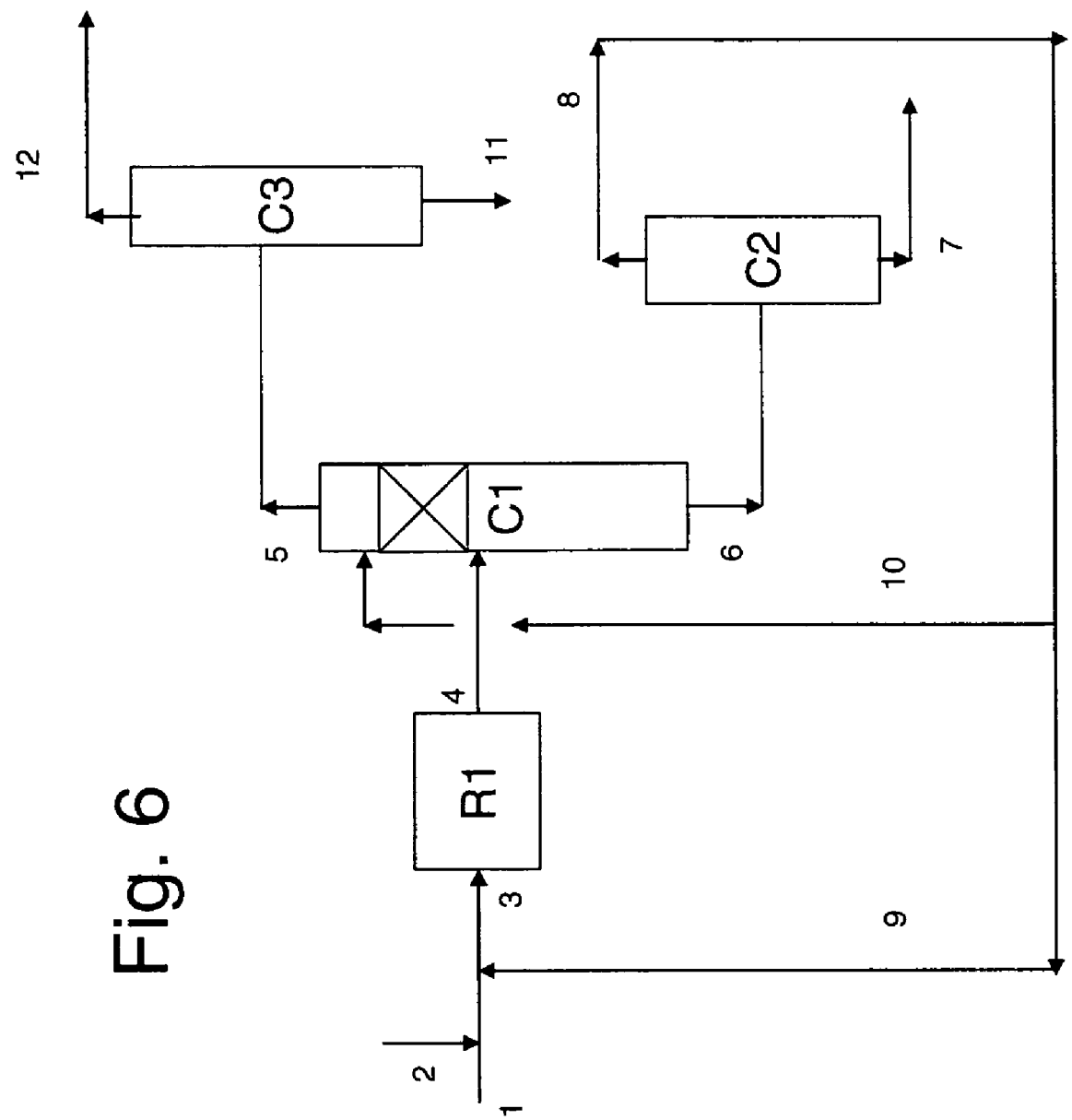
FIG. 6 shows a process scheme in which an azeotropic product is sent to a head stream of a catalytic distillation column.

A further option, shown in FIG. 6, consists in sending this azeotropic product to the head stream of the catalytic distillation column together with the $C_4$ products and in using a new column (C3) to recover the $C_5$/TBA azeotropic product at the bottom (11) and $C_4$ products at the head (12).

Figure 7:
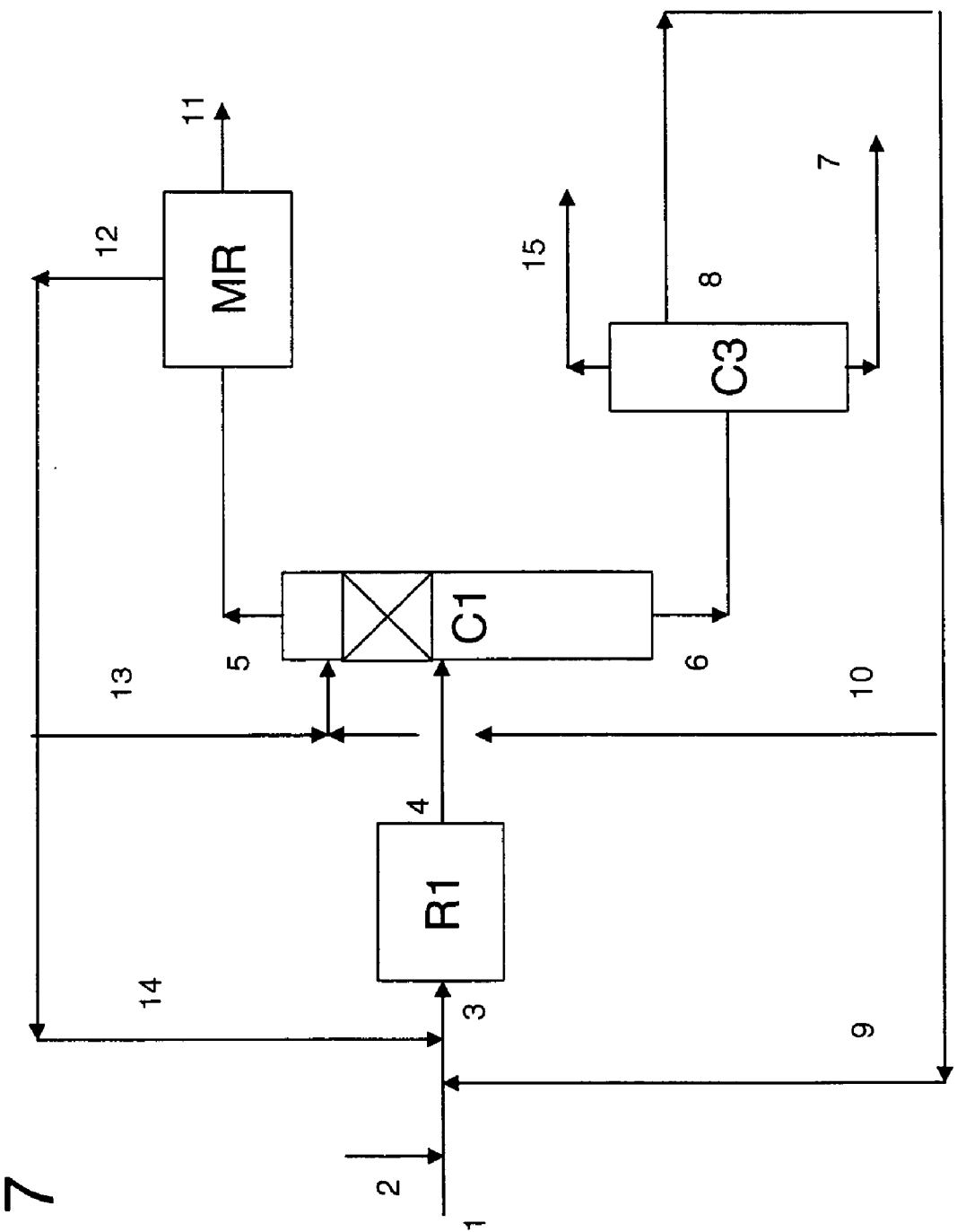
FIG. 7 shows a process scheme that includes a mixture of oxygenated products.

FIG. 7 shows a possible process scheme when a mixture of oxygenated products, consisting of alkyl ether (MTBE), linear alcohol (Methanol) and branched alcohol (TBA), is used. In this case, the stream (1) containing isobutene, together with the reintegration feeding of methanol and TBA (or water) (2) and the recycled streams of oxygenated products (MTBE and TBA) (9) and methanol (14), is sent to the first reaction step (R1), which can consist of one or more reactors, in which the $C_4$ iso-olefin is selectively converted to dimers.

The effluent (4) from the first reaction step is sent to catalytic distillation (C1), which represents the second reaction step, together, possibly, with the recycled streams of oxygenated products (10) and methanol (13). A stream (5) is collected from the head of this column, essentially containing $C_4$ hydrocarbons and methanol, which is fed to a unit for the recovery of the alcohol (MR) which can consist, for example, of an adsorption system on molecular sieves, or a water washing column. In both cases, the alcohol recovered (12) can be sent back to the two reaction steps (streams 13 and 14), whereas the hydrocarbon stream (11) can be used in subsequent operations.

The bottom stream (6) of the column C1 is sent to a further separation column (C3) wherein a stream (15) containing the $C_5$/branched alcohol azeotropic product is collected at the head, a stream (8) essentially containing MTBE, TBA and dimers, as side cut, which is recycled to the two reaction steps (streams 9 and 10), whereas the reaction product (7), essentially consisting of dimers, trimers and small quantities of oligomers is recovered from the bottom.

The invention claimed is:

1. A process for the production of high-octane hydrocarbon compounds comprising a selective dimerization of isobutene comprised in a stream also comprising $C_5$ hydrocarbons, wherein:
   the selective dimerization is carried out with acid catalysts in two distinct steps wherein the first step consists of contacting the stream with one or more fixed bed reactors and the second step consists of catalytically distilling the stream;
   wherein the selective dimerization is carried out in the presence of one or more oxygenated products selected from a branched alcohol alone or in a blend with linear alcohols and alkyl ethers, wherein the branched alcohol forms an azeotropic mixture with the $C_5$ hydrocarbons, in such a quantity as to have in the feeding, in the case of the presence of a branched alcohol alone, a molar ratio of oxygenated product/isobutene higher than 0.005, in the case of the presence of a branched alcohol in a blend, a molar ratio of oxygenated product/isobutene higher than 0.01; and
   a $C_5$/branched alcohol azeotropic separation step is carried out.

2. The process according to claim 1, wherein the first reaction step is carried out at a reaction temperature ranging from 30 to 120° C., at a pressure lower than 5 MPa and feeding space velocities lower than 30 $h^{-1}$.

3. The process according to claim 2, wherein the feeding space velocities range from 1 to 15 $h^-$.

4. The process according to claim 1, wherein the branched alcohol has a number of carbon atoms ranging from 3 to 6.

5. The process according to claim 4, wherein the branched alcohol is selected from tert-butyl alcohol or tert-amyl alcohol.

6. The process according to claim 1, wherein water is fed to the reaction, the water being capable of forming the branched alcohol by reacting with the tertiary olefin under the reaction conditions.

7. The process according to claim 1, wherein the linear alcohol has a number of carbon atoms ranging from 1 to 6.

8. The process according to claim 7, wherein the linear alcohol is selected from methanol and/or ethanol.

9. The process according to claim 1, wherein the alkyl ether has a number of carbon atoms ranging from 5 to 10.

10. The process according to claim 9, wherein the alkyl ether is selected from MTBE, ETBE, MSBE, ESBE, TAME, TAEE or mixtures thereof.

11. The process according to claim 1, wherein the oxygenated product is the branched alcohol alone, comprising:
   a) feeding a $C_4$-$C_5$ hydrocarbon cut comprising isobutene to the first reaction step (consisting of one or more reactors), together with one or more streams comprising oxygenated products;
   b) using a catalytic distillation column as second reaction step, wherein isobutene conversion is completed, in addition to separation of reagents/products;
   c) recovering a $C_5$ hydrocarbon/branched alcohol azeotropic product, in one or more catalytic fractionation columns, as head stream, side cut or bottom stream;
   d) recycling the stream comprising the oxygenated products and optionally comprising the reintegrated oxygenated products, to the two reaction steps; and
   e) optionally, recycling part of the $C_4$ products to the first reaction step, in order to maximize the isobutene conversion.

12. The process according to claim 11, wherein the recovering of the $C_5$/branched alcohol azeotropic product can be effected starting from blends of:
   a. $C_5$-oxygenated products—reaction product, wherein the $C_5$ hydrocarbons are recovered as an azeotropic compound with the branched alcohol, as head effluent, using a scheme based on one or two fractionation columns;
   b. $C_4$-$C_5$-oxygenated products—reaction product, wherein the $C_5$ hydrocarbons are recovered as an azeotropic compound with the branched alcohol as side cut of a catalytic distillation column from whose head $C_4$ products are recovered and from the bottom a blend containing the oxygenated products and the reaction product;
   c) $C_4$-$C_5$-oxygenated products, wherein the $C_5$ hydrocarbons are recovered as an azeotropic compound with the branched alcohol, as bottom effluent of a fractionation column from whose head the $C_4$ products are recovered.

13. The process according to claim 11, wherein the first reaction step is carried out in at least one of a fixed bed reactor, a tubular reactor and an adiabatic reactor.

14. The process according to claim 11, wherein a molar ratio of oxygenated product/isobutene is lower than 0.6.

15. The process according to claim 1, wherein the oxygenated product is the branched alcohol in a blend with linear alcohols and alkyl ethers, comprising:
   a) feeding a $C_4$-$C_5$ hydrocarbon cut comprising isobutene to the first reaction step, together with one or more streams comprising the oxygenated products;
   b) using a catalytic distillation column as second reaction step, wherein isobutene conversion is completed in addition to a separation of reagents/products;
   c) separating $C_4$ products and $C_4$/linear alcohol azeotropic products from the $C_5$ hydrocarbons, from remaining oxygenated compounds and from the hydrocarbon product, in one or more catalytic distillation columns;
   d) recovering the linear alcohol from the azeotropic product with the $C_4$ compounds, by means of conventional processes such as water washing or adsorption on inorganic solids;
   e) recovering the $C_5$/branched alcohol azeotropic product, in one or more catalytic fractionation columns, as head stream, side cut or bottom stream;
   f) recycling the stream comprising the oxygenated products (branched alcohol and ether) and optionally comprising the reintegrated oxygenated products and the linear alcohol recovered, to the two reaction steps;
   g) optionally, recycling part of the $C_4$ products to the first reaction step to maximize the isobutene conversion.

16. The process according to claim 15, wherein the recovering of the $C_5$/branched alcohol azeotropic product can be effected starting from blends of:
   a) $C_5$-oxygenated products (ethers and branched alcohols)—reaction product, wherein the $C_5$ hydrocarbons are recovered as an azeotropic compound with the branched alcohol, as head effluent, using a scheme based on one (recovery of the remaining oxygenated products as side cut) or two fractionation columns;

b) $C_5$-oxygenated products (ethers and branched alcohols)—dimers, in which the $C_5$ hydrocarbons are recovered as an azeotropic product with branched alcohol as head effluent of a fractionation column;
c) $C_4$-$C_5$-oxygenated products (ethers and linear and branched alcohols)—reaction product, effluent from a reaction step, wherein the $C_5$ hydrocarbons are recovered as an azeotropic compound with the branched alcohol as side cut of a fractionation column from whose head the $C_4$/linear alcohol azeotropic product and optionally the $C_4$ products are recovered, whereas a mixture containing the oxygenated products and the reaction product is recovered at the bottom;
d) $C_4$-$C_5$-oxygenated products (linear and branched alcohols) wherein the $C_5$ hydrocarbons are recovered as an azeotropic compound with the branched alcohol as bottom effluent of a fractionation column from whose head the azeotropic product $C_4$/linear alcohol and optionally $C_4$ products are recovered.

17. The process according to claim 15, wherein the first reaction step is carried out in one or more of a traditional adiabatic reactor, a boiling point adiabatic reactor, and an expanded bed adiabatic reactor.

18. The process according to claim 15, wherein a molar ratio of oxygenated product/isobutene is lower than 0.7.

19. The process according to claim 11, wherein the $C_5$/branched alcohol azeotropic product is mixed with the reaction product.

20. The process according to claim 1, wherein, in the case of concentrated isobutene streams, a charge is diluted with $C_4$-$C_7$ hydrocarbons.

21. A process for producing a high-octane hydrocarbon composition, comprising:
dimerizing isobutene present in a hydrocarbon stream comprising one or more $C_5$ hydrocarbons by contacting the hydrocarbon stream with one or more acid catalysts in one or more fixed bed reactors to form a dimerized hydrocarbon stream comprising one or more $C_5$/branched alcohol azeotropes; then
catalytically distilling the dimerized hydrocarbon stream to form a catalytically distilled hydrocarbon stream; then
separating a $C_5$/branched alcohol azeotrope from the catalytically distilled hydrocarbon stream;
wherein the hydrocarbon stream is dimerized in the presence of one or more oxygenated products selected from the group consisting of a branched alcohol, a blend of a branched alcohol with one or more linear alcohols, a blend of a branched alcohol with one or more alkyl ethers, and a blend of a branched alcohol with one or more linear alcohols and one or more alkyl ethers,
wherein the hydrocarbon stream comprises the isobutene and the oxygenated product in an oxygenated product/isobutene molar ratio of greater than 0.005 when the oxygenated product consists of a branched alcohol; or the hydrocarbon stream comprises the isobutene and the oxygenated product in an oxygenated product/isobutene molar ratio of greater than 0.01 when the oxygenated product is a blend of the branched alcohol with one or more of the linear alcohol and the alkyl ether.

22. The process according to claim 21, wherein the hydrocarbon stream is dimerized at a temperature of 30-120° C.; at a pressure of lower than 5 MPa; and at a feeding space velocity of lower than 30 $h^{-1}$.

23. The process according to claim 21, wherein the branched alcohol has from three to six carbon atoms.

24. The process according to claim 21, wherein the branched alcohol is at least one selected from the group consisting of tert-butyl alcohol and tert-amyl alcohol.

25. The process according to claim 21, further comprising:
feeding water to the stream during the dimerizing, and
forming the branched alcohol by reacting a tertiary olefin with water during the dimerizing.

26. The process according to claim 21, wherein the oxygenated product comprises one or more linear alcohols having from one to six carbon atoms.

27. The process according to claim 21, wherein the oxygenated product comprises at least one linear alcohol selected from the group consisting of methanol and ethanol.

28. The process according to claim 21, wherein the oxygenated product comprises one or more alkyl ethers having from five to ten carbon atoms.

29. The process according to claim 21, wherein the oxygenated product comprises one or more alkyl ethers selected from the group consisting of MTBE, ETBE, MSBE, ESBE, TAME and TAEE.

30. The process according to claim 21, wherein the oxygenated product consists of a branched alcohol and the process comprises:
a) feeding a $C_4$-$C_5$ hydrocarbon cut comprising isobutene to a fixed bed reactor together with one or more other streams comprising the oxygenated product during the dimerizing;
b) converting the isobutene and the $C_4$-$C_5$ hydrocarbon cut during the catalytic distilling and then separating the converted $C_5$-$C_4$ hydrocarbon cut;
c) separating the $C_5$ hydrocarbon/branched alcohol azeotrope in one or more catalytic fractionation columns as at least one of a headstream, a side cut and a bottom stream;
d) recovering the $C_5$ hydrocarbon/branched alcohol azeotrope separated in (c) and, optionally, recycling one or more reintegrated oxygenated products to the dimerizing and the catalytically distilling; and
e) optionally recycling a portion of a $C_4$ dimerization product to the dimerizing.

31. The process according to claim 30, wherein the recovering meets at least one of the following conditions:
(a) the $C_5$/branched alcohol azeotrope is recovered as a head effluent from one or two fractionation columns;
(b) the $C_5$ hydrocarbon/branched alcohol azeotrope is recovered as a side cut of a catalytic distillation column producing a $C_4$ head product and a bottom product comprising a blend of the oxygenated products and the catalytically distilled product; and
(c) the $C_5$ hydrocarbon/branched alcohol azeotrope is recovered as a bottom effluent of a fractionation column having a head forming a $C_4$ product.

32. The process according to claim 21, wherein the oxygenated product comprises a blend of the branched alcohol, the linear alcohol and the alkyl ether, and wherein the process comprises:
(a) feeding a $C_4$-$C_5$ hydrocarbon cut comprising isobutene to the selective dimerization in combination with one or more streams comprising the oxygenated product;
b) converting the isobutene and the $C_4$-$C_5$ hydrocarbon cut during the catalytic distilling and then separating the converted $C_5$-$C_4$ hydrocarbon cut;
c) separating the $C_5$ hydrocarbon/branched alcohol azeotrope in one or more catalytic fractionation columns as at least one of a headstream, a side cut and a bottom stream;
(d) recovering the linear alcohol is from the $C_4$/linear alcohol azeotrope;

(e) recovering the $C_5$ hydrocarbon/branched alcohol azeotrope in one or more catalytic fractionation columns as a least one of a head stream, a side cut or a bottom stream; and (f) recycling the oxygenated products to at least one of the catalytic distillation and the selective dimerization.

* * * * *